(12) United States Patent
Niederbacher

(10) Patent No.: US 12,104,147 B2
(45) Date of Patent: Oct. 1, 2024

(54) BIOGAS PLANT FOR FERMENTING ORGANIC MATERIALS AND FOR GENERATING BIOGAS

(71) Applicant: Michael Niederbacher, Bruneck (IT)

(72) Inventor: Michael Niederbacher, Bruneck (IT)

( * ) Notice: Subject to any disclaimer, the term of this patent is extended or adjusted under 35 U.S.C. 154(b) by 641 days.

(21) Appl. No.: 17/284,519

(22) PCT Filed: Oct. 2, 2019

(86) PCT No.: PCT/EP2019/076683
§ 371 (c)(1),
(2) Date: Apr. 12, 2021

(87) PCT Pub. No.: WO2020/074336
PCT Pub. Date: Apr. 16, 2020

(65) Prior Publication Data
US 2022/0162532 A1 May 26, 2022

(30) Foreign Application Priority Data
Oct. 12, 2018 (DE) .............. 10201800804.7

(51) Int. Cl.
*C12M 1/107* (2006.01)
*C12M 1/00* (2006.01)

(52) U.S. Cl.
CPC ............ *C12M 21/04* (2013.01); *C12M 23/52* (2013.01); *C12M 23/58* (2013.01); *C12M 47/10* (2013.01)

(58) Field of Classification Search
CPC ...... C12M 21/04; C12M 23/52; C12M 23/58; C12M 47/10

USPC ....................................... 435/289.1
See application file for complete search history.

(56) References Cited

U.S. PATENT DOCUMENTS

2013/0183705 A1 * 7/2013 Barclay ................ C12N 1/12
435/292.1

FOREIGN PATENT DOCUMENTS

DE 4419795 A1 * 6/1995 ............ B63B 35/00
KR 20150052726 A * 5/2015

OTHER PUBLICATIONS

DE-4419795-A1 Machine English Translation (Year: 1995).*
KR20150052726A Machine English Translation (Year: 2015).*

* cited by examiner

*Primary Examiner* — Michael L Hobbs
*Assistant Examiner* — Lenora A Abel
(74) *Attorney, Agent, or Firm* — Southeast IP Group LLC; Thomas L. Moses

(57) ABSTRACT

The invention relates to a biogas plant for fermenting organic materials and for generating biogas, having a plurality of containers and/or tanks, which form at least one slurry store (7), at least one fermenter container (8) downstream of the slurry store (7), at least one post-fermenter container (9) downstream of the fermenter container (8) and/or at least one final storage container (10) downstream of the fermenter container (8). According to the invention it is provided that the entire functional biogas plant is, as a floating biogas plant, a component of a one-part or of a multi-part connected floating body.

7 Claims, 3 Drawing Sheets

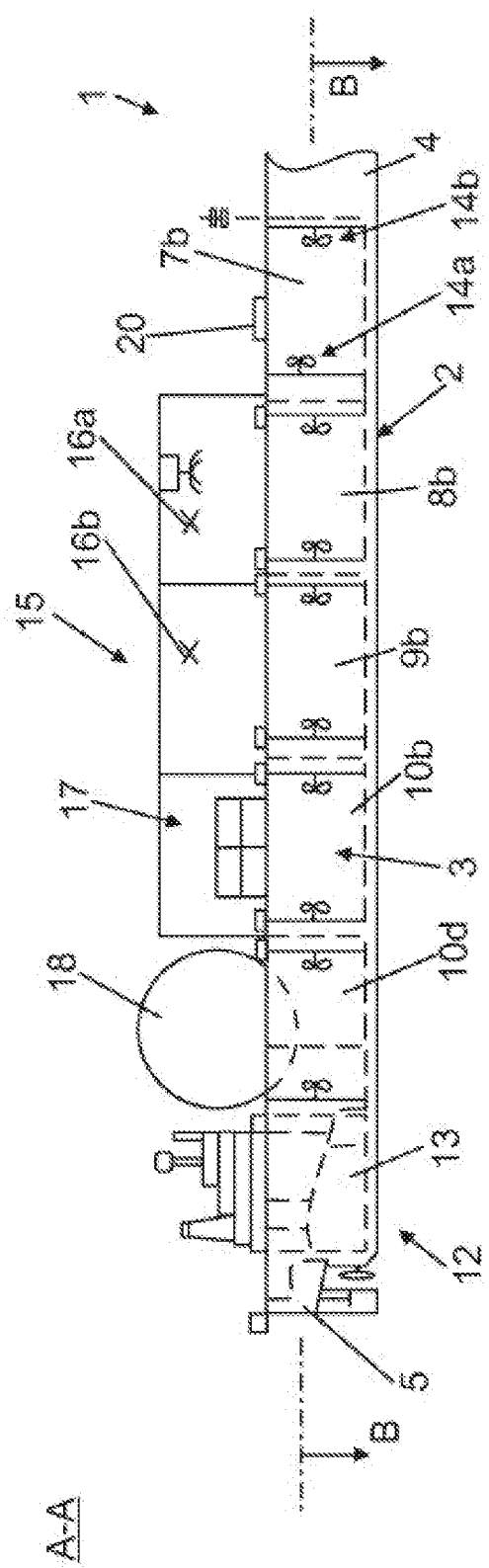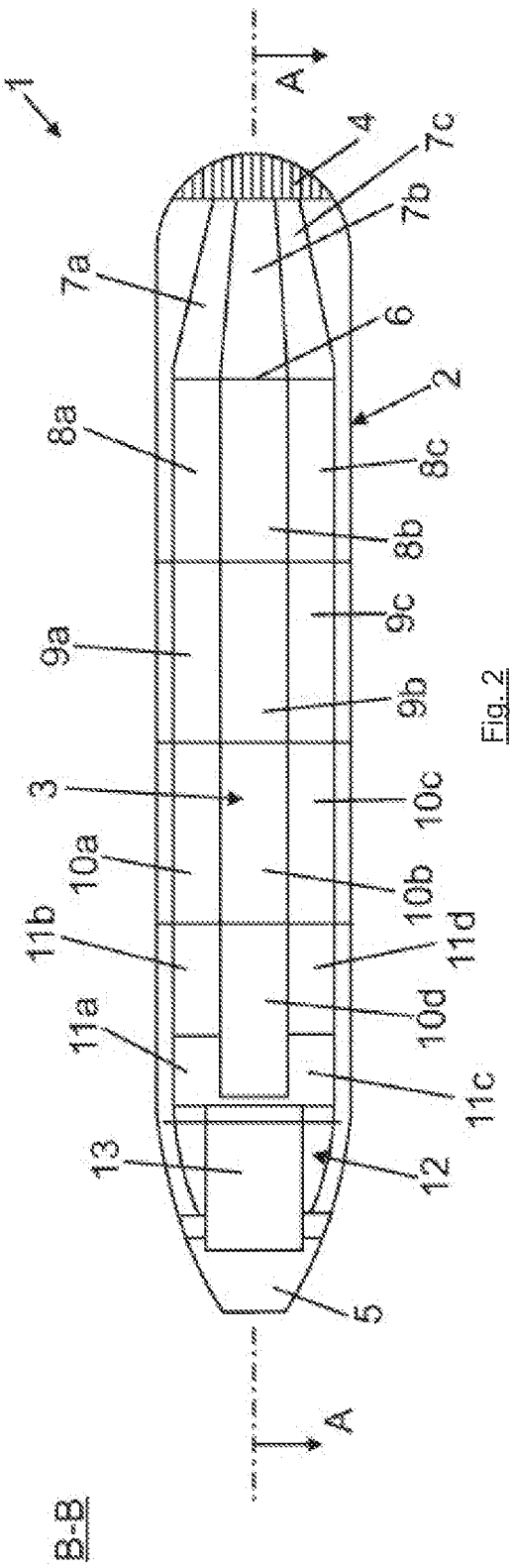

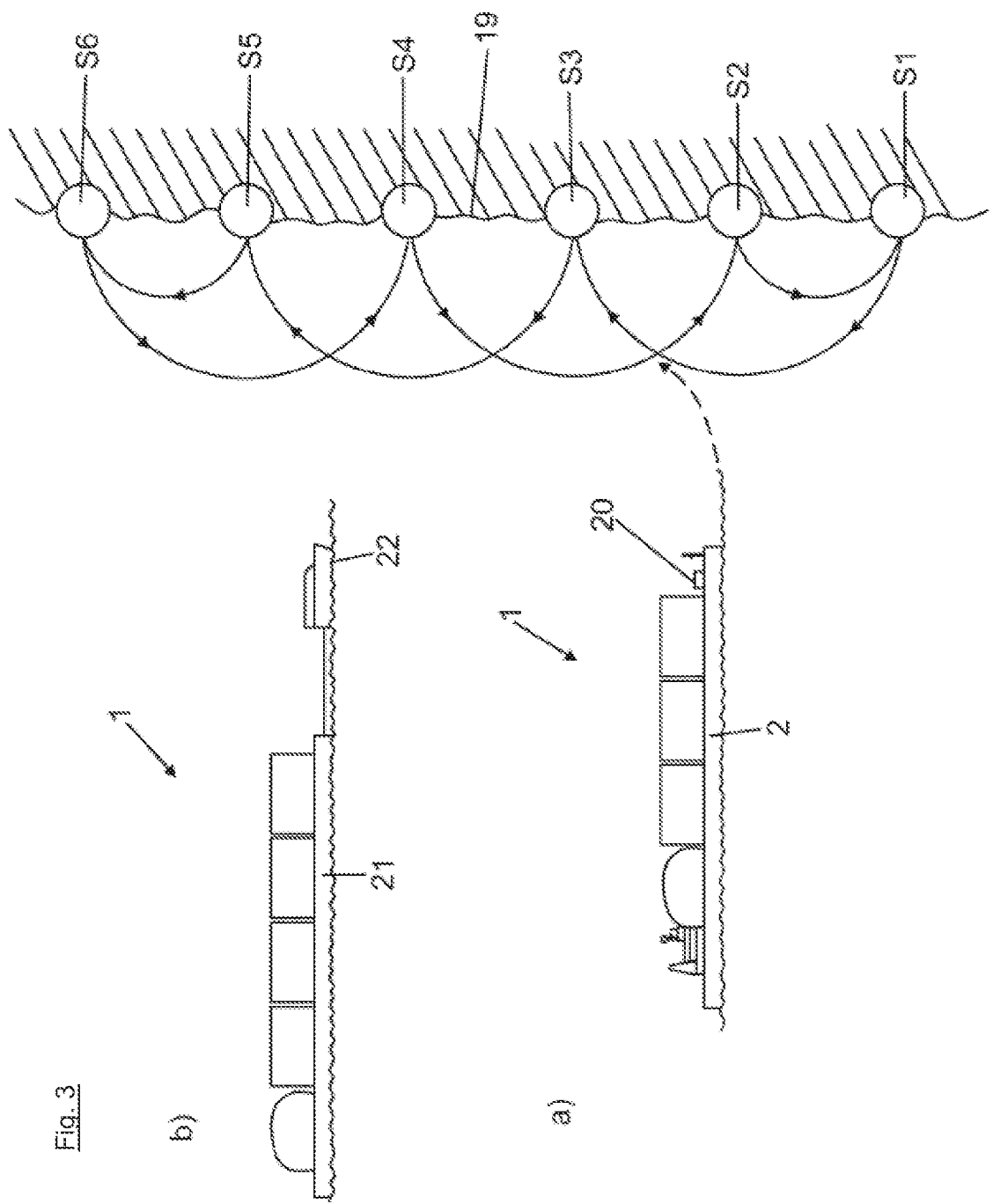

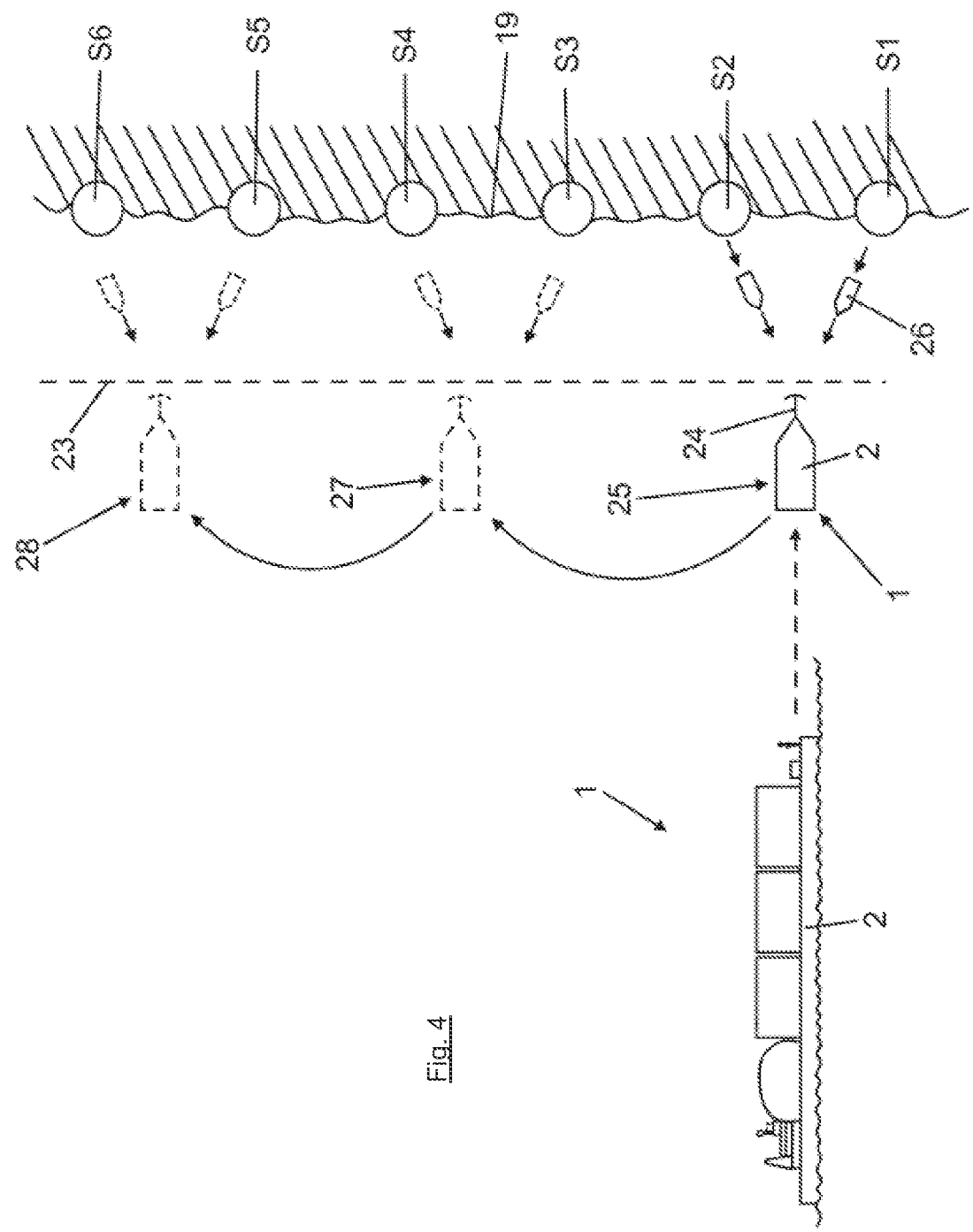

BIOGAS PLANT FOR FERMENTING ORGANIC MATERIALS AND FOR GENERATING BIOGAS

The invention relates to a biogas plant for, preferably continuously, fermenting organic materials and for generating biogas.

In such generally known, generic biogas plants, a fermentation process takes place in which organic materials as biomass, in particular agricultural and household organic residues, are gasified. Conventional biogas plants have a slurry store for the collecting and processing of organic materials for charging a downstream fermenter container in which the fermentation or gasification process is carried out under aerobic or anaerobic conditions by microorganisms. Post-fermentation is usually carried out in a downstream post-fermenter container, which is followed by a final storage container for collecting fermentation residues. If necessary, such a biogas plant can have further containers and tanks, for example for process water or for collecting non-fermentable contaminants. The biogas generated in the fermenter containers as biomethane is withdrawn and usually used in a biogas plant to generate energy, for example as heating gas or to generate electricity in downstream gas-fired internal combustion engines with electric generators.

The known biogas plants are stationary plants, the containers of which are either embedded in the ground or designed as elevated containers. The biomass for fermentation, for example maize, grass, manure, liquid manure, fermentation sludge, slaughterhouse waste, household organic residues, etc. are transported to the stationary biogas plants in suitable vehicles and processed there.

In cities, particularly in large cities, there are considerable amounts of garbage, the most environmentally friendly disposal of which is becoming increasingly difficult. Landfills require an unfavorably large amount of space and have an unpleasant odor. Waste incineration plants are not environmentally friendly due to the pollutants they emit. Households as well as municipal waste disposal companies collect so-called organic waste separately from normal residual waste, which is then transported to any stationary biogas plant for fermentation. Such biogas plants require a relatively large area and can only be located far outside of cities due to the dense population in cities and the mostly high land prices and possibly the odor nuisance, which results in unfavorably long transport routes. In addition, the construction of new biogas plants in urban regions is usually no longer possible due to a lack of suitable land and often considerable resistance from citizens.

The above problems also particularly affect coastal cities, particularly in southern latitudes, where waste disposal has been known to have been a major problem for many years. Because of the high summer temperatures, the disposal of organic waste is particularly critical. The term "organic waste" is understood in this case in a very general way as fermentable biomass which may be mixed with contaminants and which, for example, occurs in households and can contain leftovers, as well as commercial organic waste from hotels, slaughterhouse waste, etc.

The object of the invention is to develop a generic biogas plant in such a way that an environmentally friendly, economically effective, and citizen-acceptable disposal of organic waste from coastal cities or cities near the coast becomes possible. Another object of the invention is to propose a method for converting an oil tanker. Another object is to show a method for operating a biogas plant according to the invention.

The object with regard to the further development of a generic biogas plant is achieved with the features of claim 1. Advantageous configurations are the subject of the subclaims.

According to claim 1, a biogas plant for, preferably continuously, fermenting organic materials and for generating biogas is provided, which has a plurality of containers and/or tanks, which form at least one slurry store, at least one fermenter container downstream of the slurry store, at least one post-fermenter container downstream of the fermenter container and/or at least one final storage container downstream of the fermenter container. According to the invention it is provided that the entire functional biogas plant is, as a floating biogas plant, having the at least one slurry store, the at least one fermenter container, the at least one post-fermenter container and/or the at least one final storage container, a component of a one-part floating body or a component of a multi-part, connected floating body. It is further provided according to the invention that the one-part or multi-part floating body has its own traction drive and/or a device for docking a towing vehicle and/or a device for mooring in a port and/or a device for docking or mooring a transport ship, and/or an anchor device. Such a biogas plant is intended in particular for operational successive journeys and relocations of the floating biogas plant to a plurality of ports of coastal cities and/or to locations in the water in coastal regions (or coastal regions of coastal cities), preferably outside a 12-mile zone, in particular for receiving the organic waste arising in the ports or provided there, preferably from the shore, or for receiving the organic waste delivered to the water-side locations by means of transport ships and for preferably continuously fermenting and preferably continuously generating biogas during port stays and/or stopovers and/or during journeys. This means that the floating biogas plant can be relocated in successive journeys to a plurality of ports in coastal cities or to locations in the water, in particular to anchorages, in order to pick up organic waste there and feed it to the fermentation process with its preferably continuous fermentation and preferably continuous generation of biogas during the stays and/or the journeys. The locations in the water can be specified by their coordinates, for example. Where possible, the floating biogas plant can then also be anchored there; if this is not possible, the floating biogas plant can temporarily stay in this region. To clarify, it should be mentioned again that the water-side locations are locations in the water that are outside of harbors, for example preferably outside the 12-mile zone.

This allows for an environmentally friendly and energetically effective disposal of organic waste from coastal cities or, if necessary, from cities near the coast, without having to build and operate a separate biogas plant in each of these cities with the difficulties to be expected from lengthy approval procedures and against resistance from citizens' initiatives. In addition, the floating biogas plant can take up and pick up organic waste at regular, relatively short intervals of, for example, one week, so that only a relatively small amount of organic waste of one week has to be collected and made available.

In the case of a one-part floating body, the individual components of the floating biogas plant can be arranged on the floating body and/or integrated into the floating body. In the case of a multi-part, connected floating body, the individual components of the floating biogas plant can be distributed over the multiple floating body parts, in particular can be arranged on the respectively assigned floating body part and/or can be integrated into the respectively assigned floating body part.

The floating biogas plant further preferably has at least one container and/or tank, in particular for process water and/or contaminants.

The floating biogas plant can also particularly preferably have a pre-processing means for organic waste, wherein the organic waste can also contain contaminants, in particular sand, plastics material parts, paper/cardboard, etc. This pre-processing means is preferably designed in such a way that it can separate the organic materials as fermentable biomass from the organic waste, the biomass then being fed to the fermentation process. In the case of a port stay, the separated contaminants can be brought to shore and/or in the case of a water-side stopover onto a transport ship. Alternatively or additionally, contaminants, in particular plastics material parts and/or paper/cardboard, can at least partially also be used to generate energy through combustion/gasification in the biogas plant. Such a pre-processing means for separating contaminants and fermentable biomass can, however, also be built and operated on shore in the port region or decentrally, so that only organic, fermentable materials are absorbed by the floating biogas plant.

In a particularly preferred embodiment, the floating biogas plant also has at least one biogas processing device for processing the biogas produced. This is preferably formed by a means for liquefying the biogas to liquid natural gas (LNG) and a liquid gas tank (LNG tank). As an alternative or in addition, the processing means can be formed by a means for generating CNG (compressed natural gas) and a gas tank, in particular a high-pressure tank, since the CNG is usually a gas compressed to, for example, approximately 200 to 250 bar. The liquid natural gas and/or CNG generated in the floating biogas plant can also be used, for example, as fuel, to operate the biogas plant. In this case, it can be particularly advantageous that the traction drive of the floating biogas plant has a gas engine which is operated with part of the gas produced. As a result, the floating biogas plant is largely self-sufficient and independent of an external energy supply.

Alternatively or additionally, provision can also be made for the processing means to be in the form of a power plant, preferably a combined heat and power plant, in which electrical power and/or heat can be generated. With such a power plant, for example, self-generated electricity can be generated to the extent that is required to operate the biogas plant, for example to operate units or auxiliary units of the biogas plant, such as pumps, heaters, agitators, etc. and/or heat can be generated to the extent that it is required to operate the biogas plant, such as, for example, to heat the fermenter, to heat service water, etc. In connection with such a power plant, the floating biogas plant can optionally also have a traction drive with an electric machine, in particular with an electric motor, which can be operated with generated electricity with the interposition of at least one storage battery.

In particular, for a uniform distribution of the organic materials, for example in the fermenter sludge or to prevent solids from sticking to the container walls, it can be provided that at least one agitator device, is arranged, preferably as a height-adjustable agitator device and/or as an agitator with a propeller, in at least some of the containers of the floating biogas plant, in particular in the at least one slurry store and/or in the at least one fermenter container and/or in the at least one post-fermenter container and/or in the at least one final storage container.

Fermentation residues can preferably be pumped into sewage treatment plants on shore or discharged into the sea. For example, the fermentation residues can be discharged into the sea, particularly after a solid-liquid separation. By separating contaminants such as sand, plastics material, etc. before the fermentation process and afterwards in a solid-liquid separation system (separator), for example, it can be ensured that no contaminants get into the sea. Only organic residues (as fish feed, so to speak) are discharged into the sea.

The one-part floating body or the multi-part, connected floating body can be designed as a raft-like pontoon structure, for example in such a way that the containers, tanks, and additional devices of the biogas plant are attached to it. Such pontoon structures can in particular be pulled and relocated by a towing vehicle. Such a relatively simple system is particularly suitable for calm waters and smaller relocation routes between ports to be approached and possibly smaller organic waste quantities with a correspondingly smaller biogas plant.

In contrast, a much more functional and preferred embodiment of a floating biogas plant is that a one-part floating body is the hull of a seaworthy ship equipped with a traction drive, wherein the components of the floating biogas plant, in particular the at least one slurry store, the at least one fermenter container, the at least one post-fermenter container, and/or the at least one final storage container, and possibly further containers and/or tanks can be arranged in the hull with partial use of the outer hull walls. In ship superstructures further additional means, such as at least one biogas processing device, are arranged in particular in the form of a device for liquefying the biogas to liquid natural gas together with a liquid natural gas tank and/or in the form of a device for generating CNG (compressed natural gas) together with a gas tank and/or in the form of a power plant and/or at least one pre-processing means for organic waste, whereby, for example, the liquid natural gas tank can also be arranged in the hull.

Furthermore, the hull can be insulated on the inside or outside in order to minimize the heat losses through the hull.

As an extremely cost-effective solution for the production of a floating biogas plant in the form of a seaworthy ship, in particular as a steel ship, a converted, preferably double-walled oil tanker that has been discarded from oil transport is proposed, whereby present oil tanks are usable at least partially as containers and/or tanks, in particular as plant containers and/or process tanks. The double-walled structure can be used to advantage here for container insulation and is also a substantial safety element when used in a biogas plant, as it protects against leakage of liquids, such as fermentation residue, in the event of leaks in the inner wall. Due to the steel construction that is already present, it is relatively simple and inexpensive to manufacture the containers required for the fermentation process in a suitable size, if necessary, by welding steel walls into the steel construction.

A suitable spatial division in such a ship is obtained if, from the bow to the stern, a plurality, for example three, adjacent slurry stores, separated by bulkheads, and correspondingly a plurality, for example three, adjacent fermenter containers or tanks, a plurality, for example, three, adjacent post-fermenter containers or tanks, a plurality, for example three, adjacent, possibly downstream, final storage containers or tanks and possibly a plurality, for example four, further containers or tanks, in particular for process water and contaminants, as well as the ship's propulsion system are arranged one after the other in the hull. The means for processing organic waste, for liquefying biogas and, if necessary, for burning contaminants, for drying and pelletizing and a liquid natural gas tank can then be arranged in superstructures above.

Furthermore, a ship and a raft-like pontoon structure are claimed, which have an entire, functional biogas plant.

A method for converting a discarded oil tanker into a floating biogas plant as described above is also claimed.

In addition, a method for operating a biogas plant described above is claimed, in such a way that it successively calls at different ports of coastal cities or cities near the coast to receive the organic waste that occurs and is provided there and such that its organic materials, if necessary after processing during the port stays and during the journeys between the ports, are processed in a continuous fermentation and gasification process. Alternatively or also in combination, the floating biogas plant can temporarily also call at predetermined locations in the coastal region of coastal cities and pick up organic waste there from transport ships.

It goes without saying that any contaminants that may arise can also be brought back to shore. This is particularly the case if gasification and/or incineration is not permitted for these contaminants and the energetic recovery and/or disposal of the contaminants is also not permitted in territorial waters.

The invention is further illustrated by way of example based on a drawing, in which:

FIG. 1 is a schematic longitudinal section through an oil tanker converted into a floating biogas plant along the line A-A from FIG. 2, FIG. 2 is a schematic horizontal section along the line B-B of the oil tanker according to FIG. 1, FIG. 3 is a schematic representation for a first operating mode of the floating biogas plant, and FIG. 4 is a schematic representation for a second operating mode of the floating biogas plant.

In the sectional views of FIGS. 1 and 2, a floatable biogas plant 1 is shown, in this case only by way of example as a double-walled oil tanker 2 converted for this purpose. In the order from the bow 4 to the stern 5, three adjacent slurry stores 7a, 7b, 7c separated respectively by bulkheads 6, three adjacent horizontal containers as fermenter tanks 8a, 8b, 8c, three adjacent horizontal post-fermenter containers as post-fermenter tanks 9a, 9b, 9c, three adjacent final storage containers as final storage tanks 10a, 10b, 10c, and four further tanks 11a, 11b, 11c, 11d, in particular for process water and for collecting contaminants, and a ship's propulsion system 12 with a liquid natural gas engine 13 are arranged in the hull 3 of the oil tanker 2. A fourth final storage tank 10d is also arranged in the longitudinal direction behind the final storage tank 10b. It goes without saying that a different number of the respective containers/tanks can of course also be provided.

The sectional view according to FIG. 1 also shows two height-adjustable agitators 14a, 14b in each tank 8, 9, 10, 11 (in this case only by way of example as an agitator with one agitator blade), which are not shown in FIG. 2.

In FIG. 1, three (schematically shown) superstructures 15 are shown above the hull, which among other things can contain means 16a, 16b (not shown in detail), for processing organic waste, for incinerating contaminants, for drying, for pelleting, etc. In addition, a means 17 for liquefying biogas and/or for generating CNG (compressed natural gas) is contained in the superstructures 15, the biogas being stored in a gas tank 18 and being used partly for the gas engine 13 of the ship's propulsion system 12 and, if necessary, for other additional units. The means 17 could alternatively also be a power plant, in particular a block-type thermal power station, and the gas engine 17 could be an electrical machine.

In FIG. 3, a first operating mode for the use of a floating biogas plant 1 for the disposal of organic waste is shown in a highly schematic manner and only by way of example: For this purpose, six coastal cities S1 to S6 located at a distance on a schematized coastline 19 are shown here by way of example. The floating biogas plant 1 corresponding to the converted oil tanker 2 from FIGS. 1 and 2 is intended to call at these coastal cities S1 to S6 in a regular cycle, in this case once a week, and there in each case pick up the organic waste for a week via an acceptance opening 20 on the oil tanker 2 and then continuously feed during the port stays and the journeys between the ports of the coastal cities S1 to S6 to the running fermentation process.

For a suitable one-week cycle, starting from the coastal city S1, leaving out the next coastal city S2, the coastal city S3 can be approached, and then the coastal cities S5 and S6 can be approached. On the return journey, the coastal stands S4 and S2 left out on the outward journey can then be approached back to the coastal stand S1, so that a one-week organic waste collection is provided for each of the coastal cities S1 to S6 and the routes between the coastal cities S1 to S6 are largely adapted in the same way.

To estimate the order of magnitude, it is assumed that the coastal cities S1 to S6 have a total of around 2 million inhabitants. A suitable size for organic waste disposal is obtained when each of the tanks comprises approx. 10,000 $m^3$, i.e. a total of 150,000 $m^3$, whereby the plurality of, for example three, slurry store tanks 7a, 7b, 7c should cover a total of approx. 25,000 $m^3$, the plurality of, for example three, fermenter tanks 8a, 8b, 8c should cover a total of approx. 30,000 $m^3$, the plurality of, for example three, post-fermenter tanks 9a, 9b, 9c should cover a total of approx. 30,000 $m^3$, or the optionally available plurality of, for example four, final storage tanks 10a, 10b, 10c, 10d should cover a total of approx. 40,000 $m^3$. A suitable size for the gas tank 18 for a liquid natural gas tank is approximately 5,000 to 10,000 $m^3$. In our example, this could then possibly also be emptied to the shore about once a month. Analogously, this would of course also be possible with CNG instead of liquid natural gas, in which case the tank volume would then have to be adjusted accordingly. The magnitudes of the individual volumes are only given here by way of example and can be halved for 1 million inhabitants, for example.

In FIG. 3b, an alternative embodiment of a floating biogas plant 1 to the converted oil tanker 2 is shown with a pontoon structure 21 on which the functional units of the biogas plant with the necessary containers and additional equipment are arranged and which is relocated from a towing vehicle 22 for picking up organic waste in port facilities of coastal cities, for example, to the coastal cities S1 to S6. Obviously, this alternative according to FIG. 3b is only suitable for comparatively simple circumstances, in particular for relatively short routes in calm waters.

In FIG. 4, an alternative second operating mode of the floating biogas plant 1 is shown for the coastal cities S1 to S6 of FIG. 3, which, if necessary, can also be combined with the first operating mode with port stays. As can be seen from FIG. 4, the floating biogas plant 1 is here temporarily in the coastal region, here by way of example outside a 12-mile zone 23, at a predetermined location 25 in front of the coastal cities S1 and S2. If possible, the floating biogas plant 1 anchors there with an anchor device 24. From the coastal cities S1 and/or S2, organic waste arising there is transported by transport ships 26 to the floating biogas plant 1 for fermentation. The floating biogas plant 1 then drives to a further predetermined, temporary location 27 in the coastal region of the coastal cities S3 and S4, for example, and then accordingly further to a location 28 in the coastal region of the coastal cities S5 and S6, from where, with transport ships 26, organic waste, so to speak, is brought in an analogous manner from the mainland to the respective temporary location, which is preferably and if possible an anchorage.

What is claimed is:

1. A floating biogas plant fermenter tank system comprising:
    a seaworthy ship having overlying ship superstructure, a traction drive and a hull that includes an outer hull wall;
    a plurality of containers forming at least one slurry store;
    at least one fermenter container downstream of said slurry store;
    at least one post-fermenter container downstream of said fermenter container;
    and at least one final storage container downstream of said fermenter container;
    wherein said biogas plant fermenter tank system is a component of said ship, and
    wherein said ship further includes a at least one component selected from the group consisting of a device for docking a towing vehicle, a device for mooring in a port, a device for mooring or docking a transport ship, and a device for anchoring;
    wherein said slurry store, said fermenter container, and at least one component selected from the group consisting of said post-fermenter container and said final storage container are contained within said hull using portions of said outer hull wall as sides thereof;
    at least one biogas processing device for processing said biogas produced;
    wherein said overlying ship-superstructure includes said at least one biogas processing device in a form selected from the group of a (i) device for liquefying the biogas to liquid natural gas together with a liquid natural gas tank, or (ii) a device for generating compressed natural gas together with a gas tank.

2. The floating biogas plant fermenter tank system set forth in claim 1, further including at least one pre-processing means for organic waste for separating organic materials as fermentable biomass from contaminants; and
    wherein said contaminants are adapted to be unloaded onto a transport ship and used for energy thorough combustion or gasification.

3. The floating biogas plant fermenter tank system set forth in claim 1, wherein said traction drive includes a natural gas engine that can be operated with natural gas generated by said biogas plant fermenter tank system.

4. The floating biogas plant fermenter tank system set forth in claim 1, wherein said seaworthy ship includes a thermally insulated hull.

5. The floating biogas plant fermenter tank system set forth in claim 1, wherein said ship is a converted, double-walled, oil tanker, wherein oil tanks within said oil tanker are used as containers.

6. The floating biogas plant fermenter tank system set forth in claim 5, wherein said ship's hull houses a plurality of additional containers for processing water and contaminants, at least one intermediate final storage container or tank, and said ship's propulsion system.

7. The floating biogas plant fermenter tank system set forth in claim 1, wherein said following components are housed within said ship's hull:
    a plurality of adjacent slurry stores separated by bulkheads, a plurality of adjacent fermenter containers, a plurality of adjacent post-fermenter containers, and a plurality of adjacent final storage containers ; and
    wherein means are arranged in said ship's overlying superstructures for processing organic waste or for processing biogas for liquefying biogas, storing liquid natural gas produced, burning contaminants, drying, or pelleting.

* * * * *